US008652119B2

(12) United States Patent
Nishigishi (10) Patent No.: US 8,652,119 B2
(45) Date of Patent: Feb. 18, 2014

(54) GUIDEWIRE

(75) Inventor: Makoto Nishigishi, Nagoya (JP)

(73) Assignee: Asahi Intecc Co., Ltd., Nagoya-Shi (JP)

( * ) Notice: Subject to any disclaimer, the term of this patent is extended or adjusted under 35 U.S.C. 154(b) by 234 days.

(21) Appl. No.: 13/179,231

(22) Filed: Jul. 8, 2011

(65) Prior Publication Data

US 2012/0041421 A1 Feb. 16, 2012

(30) Foreign Application Priority Data

Aug. 10, 2010 (JP) ................................ 2010-179149

(51) Int. Cl.
*A61M 25/00* (2006.01)

(52) U.S. Cl.
USPC ......................................... 604/528; 600/585

(58) Field of Classification Search
USPC ......................................... 604/528; 600/585
See application file for complete search history.

(56) References Cited

U.S. PATENT DOCUMENTS

| 5,052,404 | A | 10/1991 | Hodgson | |
|---|---|---|---|---|
| 5,063,935 | A | 11/1991 | Gambale | |
| 5,345,945 | A * | 9/1994 | Hodgson et al. | ............... 600/585 |
| 5,377,690 | A | 1/1995 | Berthiaume | |
| 7,025,758 | B2 * | 4/2006 | Klint | ............................ 604/524 |
| 7,077,811 | B2 | 7/2006 | Vrba et al. | |
| 7,117,703 | B2 | 10/2006 | Kato et al. | |
| 8,241,230 | B2 * | 8/2012 | Brumleve et al. | ............. 600/585 |
| 2002/0151823 | A1 | 10/2002 | Miyata et al. | |
| 2002/0198468 | A1 | 12/2002 | Kato et al. | |
| 2004/0116833 | A1 | 6/2004 | Kato et al. | |
| 2008/0045908 | A1 | 2/2008 | Gould et al. | |
| 2009/0005706 | A1 | 1/2009 | Miyata et al. | |
| 2009/0112127 | A1 * | 4/2009 | Keating et al. | ................. 600/585 |
| 2010/0292613 | A1 * | 11/2010 | Nowak, Jr. | ..................... 600/585 |

FOREIGN PATENT DOCUMENTS

| EP | 0 611 073 A1 | 8/1994 |
|---|---|---|
| JP | 06-054911 | 3/1994 |
| JP | A-6-292729 | 10/1994 |
| JP | A-7-80076 | 3/1995 |
| JP | A-7-227429 | 8/1995 |
| JP | A-2001-178829 | 7/2001 |
| JP | A-2004-190167 | 7/2004 |
| JP | T 2006-511304 | 4/2006 |
| JP | A 2009-337 | 1/2009 |
| JP | A-2009-233200 | 10/2009 |

OTHER PUBLICATIONS

Nov. 16, 2011 European Search Report issued in European Patent Application No. 11172353.2.
Office Action for Japanese Patent Application No. 2010-179149 dated Aug. 31, 2012 (with English translation).

* cited by examiner

*Primary Examiner* — Max Hindenburg
*Assistant Examiner* — Renee Danega
(74) *Attorney, Agent, or Firm* — Oliff PLC (57) ABSTRACT

A guidewire having high rotational torque transmissibility and high pushing torque transmissibility and having favorable restorability is provided. The guidewire has an outer coil having a tapered coil portion constituted by at least one strand wound to decrease an outer diameter toward a front end of a core shaft and an inner coil arranged inside the outer coil. An outer diameter on a front side of the inner coil arranged on a front side of the tapered coil portion is smaller than an outer diameter on a rear side of the inner coil.

11 Claims, 5 Drawing Sheets

GUIDEWIRE

CROSS REFERENCE TO RELATED APPLICATIONS

This application is based on Japanese Patent Application No. 2010-179149 filed with the Japan Patent Office on Aug. 10, 2010, the entire content of which is hereby incorporated by reference.

TECHNICAL FIELD

The present invention relates to a medical guidewire.

BACKGROUND ART

Conventionally, several kinds of guidewires that guide a catheter or the like used by being inserted in a tubular organ such as a vessel, a digestive tract, or a ureter or an intracorporeal tissue for a treatment or examination are proposed. Examples of such guidewires include a guidewire having a coil doubly-provided at a tip portion of a core shaft (for example, refer to U.S. Pat. No. 5,345,945 and JP-T-2006-511304) and a guidewire using a stranded wire including a plurality of strands as a coil at a tip portion (for example, refer to JP-A-2009-337).

There is also a guidewire that needs to pass through a narrow lesion location such as a relatively serious stenosis of a vessel. An example of such a guidewire is a guidewire having a coil with a tapered portion and with a small outer diameter of a tip portion (for example, refer to FIG. 5 in U.S. Pat. No. 5,345,945 described above).

SUMMARY OF INVENTION

Such a guidewire is required to have high transmissibility of rotational torque to transmit rotational torque given from a proximal side of the guidewire to a front side in order to advance into a narrow lesion location. This guidewire is also required to have high transmissibility of pushing torque (axial torque) to make the front side of the guidewire advance into the lesion location appropriately in the axial direction when the guidewire is pushed in the axial direction. To heighten the transmissibility of the rotational torque and the pushing torque, it is generally thought to make a core shaft of the guidewire entirely thick to increase stiffness.

However, increasing the diameter of the core shaft to increase stiffness causes a drawback in which restorability of the guidewire is worsened. In other words, when the guidewire is pushed into the narrow lesion location and contacts with the lesion location, a drawback occurs in which a tip portion of the guidewire may be plastically deformed and may not be restored in a bent or curved state and may produce a residual angle highly possibly.

The present invention has been made to solve the foregoing drawbacks, and an object of the present invention is to provide a guidewire having high rotational torque transmissibility and high pushing torque transmissibility and having favorable restorability.

It is to be noted that the expression of "torque transmissibility" in the present description means both rotational torque transmissibility and pushing torque transmissibility unless otherwise stated.

In the present invention, the above object is solved by the following structure.

<1> An invention according to a first aspect is a guidewire comprising a core shaft; an outer coil having a tapered coil portion constituted by at least one strand wound to decrease an outer diameter toward a front end of the core shaft and surrounding a front side portion of the core shaft; an inner coil constituted by at least one strand wound, which surrounds the front side portion of the core shaft in the outer coil, and whose outer diameter on a front side arranged on a front side of the tapered coil portion is smaller than an outer diameter on a rear side; a front end joint joining a front end of the outer coil and a front end of the inner coil to the front end of the core shaft; an outer rear end joint joining a rear end of the outer coil to the core shaft; and an inner rear end joint joining a rear end of the inner coil to the core shaft further on a front side than the outer rear end joint.

BRIEF DESCRIPTION OF DRAWINGS

The foregoing and other objects, features, aspects and advantages of the invention will become more apparent from the following detailed description when taken in conjunction with the accompanying drawings.

DESCRIPTION OF EMBODIMENTS

Preferred embodiments of the present invention will be described below with reference to the accompanying drawings, in which like reference characters designate similar or identical parts throughout the several views thereof.

<1> An invention according to the first aspect is a guidewire comprising a core shaft; an outer coil having a tapered coil portion constituted by at least one strand wound to decrease an outer diameter toward a front end of the core shaft and surrounding a front side portion of the core shaft; an inner coil constituted by at least one strand wound, which surrounds the front side portion of the core shaft in the outer coil, and whose outer diameter on a front side arranged on a front side of the tapered coil portion is smaller than an outer diameter on a rear side; a front end joint joining a front end of the outer coil and a front end of the inner coil to the front end of the core shaft; an outer rear end joint joining a rear end of the outer coil to the core shaft; and an inner rear end joint joining a rear end of the inner coil to the core shaft further on a front side than the outer rear end joint.

<2> An invention according to a second aspect is the guidewire according to the first aspect, wherein the inner coil includes: a front inner coil portion which is arranged on a front side of the inner coil and constituted by at least one strand wound such that the front inner coil portion has an approximately constant outer diameter; and a rear inner coil portion which is arranged on a rear side of the inner coil, constituted by at least one strand wound such that the rear inner coil portion has an approximately constant outer diameter, and which has a larger outer diameter than the outer diameter of the front inner coil portion.

<3> An invention according to a third aspect is the guidewire according to the second aspect, wherein a diameter of the strand constituting the front inner coil portion is smaller than a diameter of the strand constituting the rear inner coil portion.

<4> An invention according to a fourth aspect is the guidewire according to the second or third aspect, wherein the front inner coil portion and the rear inner coil portion of the inner coil are joined to each other by an inner intermediate joint, and the inner intermediate joint joins the inner coil to the core shaft.

<5> An invention according to a fifth aspect is the guidewire according to the fourth aspect, wherein the outer coil has a front straight coil portion having an approximately constant outer diameter on a front side of the tapered coil portion, and the inner intermediate joint is located further on a rear side than a border between the front straight coil portion and the tapered coil portion.

<6> An invention according to a sixth aspect is the guidewire according to the fifth aspect, wherein the front straight coil portion has an open coiled portion at which coils are spaced from one another on a front side of the front straight coil portion and a close coiled portion at which coils substantially contact one another on a rear side of the front straight coil portion.

<7> An invention according to a seventh aspect is the guidewire according to any one of the second to sixth aspects, wherein at least one of the front inner coil portion and the rear inner coil portion has a hollow stranded coil made by winding a plurality of strands.

<8> An invention according to an eighth aspect is the guidewire according to the seventh aspect, wherein the rear inner coil portion is constituted by a smaller number of strands than the front inner coil portion.

<9> An invention according to a ninth aspect is the guidewire according to the first aspect, wherein the inner coil is constituted by a single coil made by winding at least one strand to have an outer diameter that gradually decreases toward the front end of the core shaft.

<10> An invention according to a tenth aspect is the guidewire according to the ninth aspect, wherein a cross-sectional area of the strand on a front side of the inner coil is smaller than a cross-sectional area of the strand on a rear side of the inner coil.

<11> An invention according to an eleventh aspect is the guidewire according to any one of the first, ninth, and tenth aspects, wherein the inner coil is a hollow stranded coil made by winding a plurality of strands.

<1> In the guidewire according to the first aspect, the outer coil has the tapered coil portion having an outer diameter that decreases toward the front end. Accordingly, the outer diameter of the front end of the guidewire is made to be smaller. Thus, the front end of the guidewire can be inserted even in a narrow stenosis. Also, the guidewire can enter the stenosis while the tapered coil portion gradually expands the stenosis.

The inner coil arranged in this outer coil has a smaller diameter on the front side than a diameter on the rear side so as to correspond to the tapered coil portion of the outer coil. Thus, even in a case where the outer diameter of the front portion of the outer coil is decreased by the tapered coil portion, the inner coil can be arranged over a long range from the rear side of the tapered coil portion to the front end of the outer coil. Accordingly, rotational torque transmissibility and pushing torque (axial torque) transmissibility can be improved by the inner coil. Also, the outer diameter of the inner coil is smaller to correspond to a part of the tapered coil portion having a smaller outer diameter. Thus, a gap is secured between them. This can prevent contact and interference between the outer coil and the inner coil and transmit rotational torque smoothly from a rear-side part of the inner coil having a larger outer diameter to a front-side part having a smaller outer diameter in a tortuous vessel or the like. This makes a rotational angle of the front side of the guidewire correspond to a rotational angle given from the proximal side of the guidewire. That is, rotation followability of the guidewire can be improved.

Further, providing the inner coil can achieve a desired tip load. Thus, when the guidewire is pushed into a stenosis, it is possible to prevent, as much as possible, the tip portion of the guidewire from being plastically deformed in a bent or curved state and thus a residual angle from being produced in the guidewire. That is, restorability of the guidewire is improved.

<2> In the second aspect of the invention, the inner coil has the front inner coil portion and the rear inner coil portion each having an approximately constant outer diameter. Thus, a sufficient gap extending in the radial direction can be secured between the inner circumferential surface of the thin front side in the tapered coil portion of the outer coil and the outer circumferential surface of the front inner coil portion. In addition, a sufficient gap extending in the radial direction can be secured between the inner circumferential surface of the thick rear side in the tapered coil portion and the outer circumferential surface of the rear inner coil portion. Thus, when the guidewire is rotated on the proximal side in a tortuous vessel or the like, inhibition of rotational torque transmission caused by contact and interference between the inner coil and the outer coil can be prevented as much as possible. Accordingly, rotation followability of the guidewire can be further improved.

Also, since the contact and interference between the tapered coil portion of the outer coil and the inner coil can be prevented, deterioration of flexibility at the tip portion of the guidewire can be prevented as much as possible.

<3> In the third aspect of the invention, the diameter of the strand constituting the rear inner coil portion located on the rear side of the inner coil is larger than the diameter of the strand constituting the front inner coil portion located on the front side of the inner coil. This can increase torque transmissibility of the rear inner coil portion. Thus, rotational torque and pushing torque transmitted from the rear side can be transmitted to the front inner coil portion efficiently. Accordingly, torque transmissibility of the guidewire can be increased.

Also, since the diameter of the strand constituting the front inner coil portion is smaller, flexibility at the tip portion of the inner coil can be improved. Consequently, flexibility at the tip portion of the guidewire can be improved.

<4> In the fourth aspect of the invention, the inner intermediate joint joining the front inner coil portion and the rear inner coil portion to each other joins the inner coil to the core shaft. Thus, rotational torque and pushing torque transmitted from the rear inner coil portion can be transmitted not only to the front inner coil portion but also to the core shaft. This can improve transmissibility of the rotational torque and the pushing torque.

<5> In the fifth aspect of the invention, the inner intermediate joint is located further on the rear side than the border between the front straight coil portion and the tapered coil portion. This obtains a structure in which the location of the inner intermediate joint does not overlap to a portion causing a stiffness change by difference in outer diameter of the outer coil. Thus, an abrupt change in stiffness of the guidewire can be prevented as much as possible. Accordingly, rotational torque and pushing torque given from the proximal side of the guidewire can be transmitted to the front side efficiently. This improves torque transmissibility.

<6> In the sixth aspect of the invention, the open coiled portion is located on the front side of the front straight coil portion. Thus, the guidewire has a highly safe structure in which higher flexibility is secured toward the front end of the guidewire.

Also, even in a case where the outer coil and the inner coil have a higher possibility to contact each other at the tip portion of the guidewire, at which the outer coil and the inner coil having smaller outer diameters overlap, curving of the outer coil and slight movement of the strands of the outer coil are allowed by the open coiled portion. Since this diminishes interference between the outer coil and the inner coil, flexibility at the tip portion of the guidewire can be maintained.

<7> In the seventh aspect of the invention, at least either the front inner coil portion and the rear inner coil portion is the hollow stranded coil made by winding the plurality of strands. This can further improve torque transmissibility. Also, the stranded coil brings about a high effect of maintenance of flexibility and a high effect of improvement in tip load. This makes it easier to thin the tip portion of the core shaft. This improves an effect of preventing the guidewire from being bent and thus a residual angle from being produced.

<8> In the eighth aspect of the invention, the number of the strands of the rear inner coil portion is smaller than the number of the strands of the front inner coil portion. This can prevent, as much as possible, the stiffness of the rear inner coil portion having the larger outer diameter from being excessively higher than the stiffness of the front inner coil portion. This can alleviate difference in stiffness occurring between the front inner coil portion and the rear inner coil portion. Thus, torque transmissibility can be improved.

<9> In the ninth aspect of the invention, the inner coil is the single coil having an outer diameter that gradually decreases toward the front end of the core shaft. Thus, rotational torque and pushing torque can be transmitted smoothly from the rear side to the front side of the inner coil. This can improve torque transmissibility.

<10> In the tenth aspect of the invention, the cross-sectional area of the strand located on the front side of the inner coil is smaller than the cross-sectional area of the strand located on the rear side. This can improve flexibility at the front portion of the inner coil.

Also, since the cross-sectional area of the strand located on the rear side of the inner coil is larger, rotational torque and pushing torque transmitted from the rear side of the guidewire can be transmitted to the front side of the guidewire efficiently. Thus, torque transmissibility of the guidewire can be heightened.

<11> In the eleventh aspect of the invention, the inner coil is the hollow stranded coil made by winding the plurality of strands. Thus, torque transmissibility of the inner coil is high. Also, the stranded coil brings about a high effect of maintenance of flexibility and a high effect of improvement in tip load. This makes it easier to thin the tip portion of the core shaft. This improves an effect of preventing the guidewire from being bent and thus a residual angle from being produced.

Figure 1:
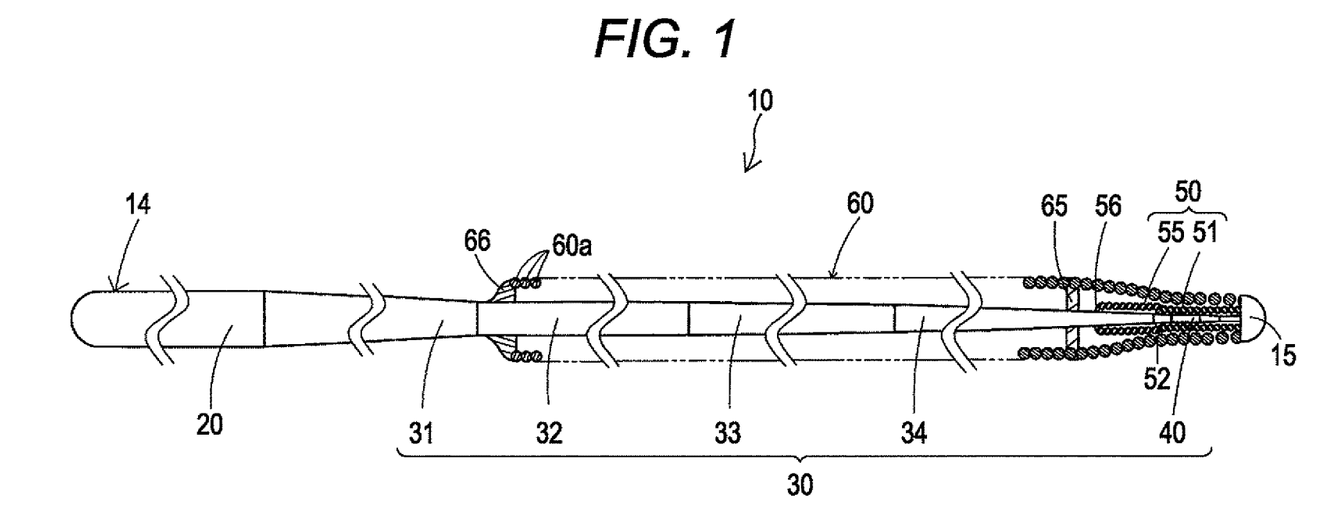
FIG. 1 illustrates an overall view of a guidewire of a first embodiment.
Figure 2:
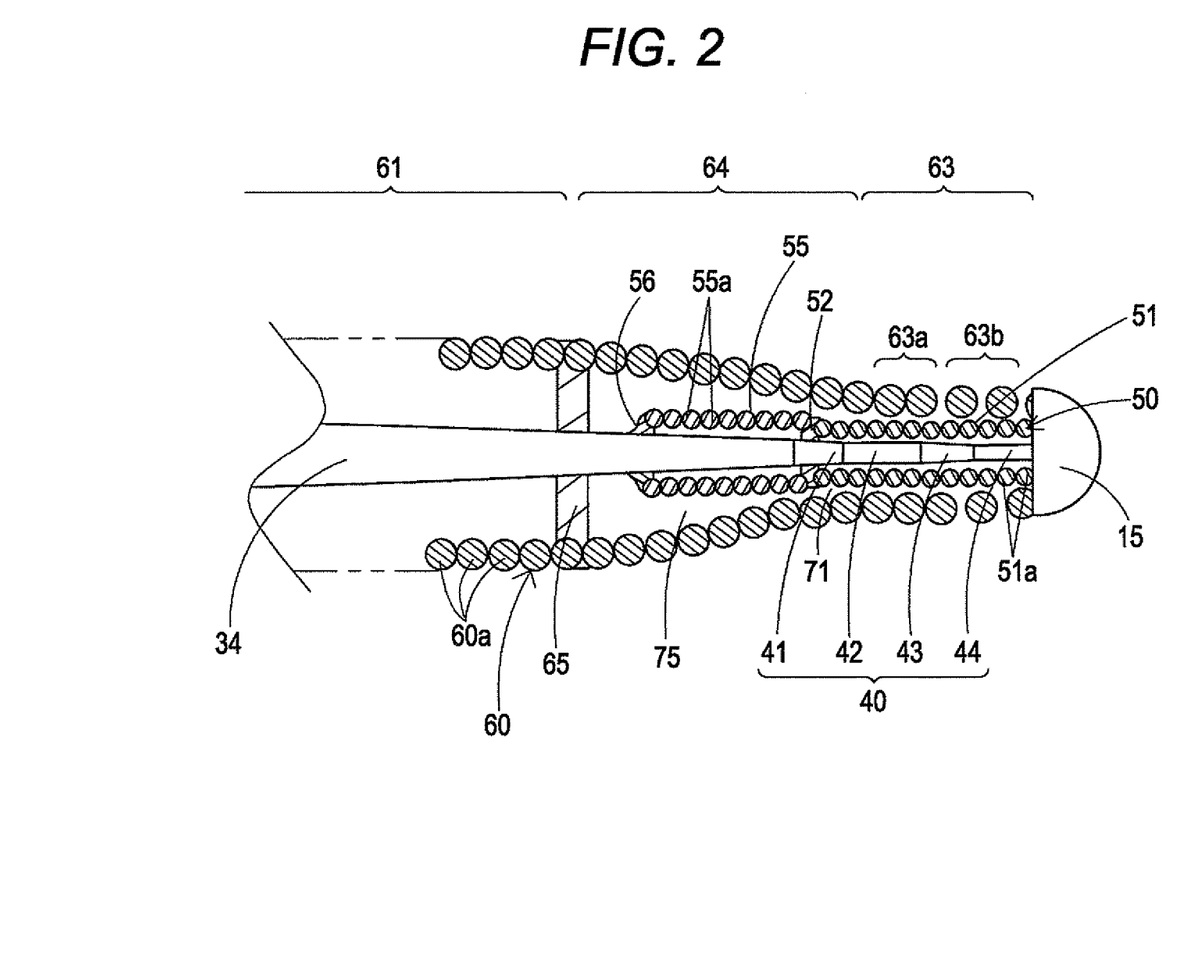
FIG. 2 illustrates a partially enlarged view of FIG. 1.

A guidewire of a first embodiment will be described with reference to FIGS. 1 and 2. In FIGS. 1 and 2, the right side is a front side (distal side) to be inserted into a body, and the left side is a rear side (proximal side, base end side) to be operated by an operator.

A guidewire 10 is used mainly for a cardiovascular treatment. The guidewire 10 is approximately 1900 mm in length in the present embodiment.

The guidewire 10 mainly has a core shaft 14, an inner coil 50, and an outer coil 60. The core shaft 14 is broadly constituted by a main body portion 20 and a front side portion 30. On the outer surface of the guidewire 10 in a predetermined range from the front end through the outer coil 60 to the main body portion 20 is applied a hydrophilic coating.

The main body portion 20 is a cylindrical part having a constant diameter and a part of the core shaft 14 excluding the front side portion 30. In the case of the present embodiment, the diameter of the main body portion 20 is set to be approximately 0.35 mm. The front side portion 30 is a thinned part of the core shaft 14. In the case of the present embodiment, the length of the front side portion 30 is approximately 260 mm.

A material for the core shaft 14 is not particularly limited. In the case of the present embodiment, stainless steel (SUS 304) is used as this material. Examples of the material other than this include a super elastic alloy such as an Ni—Ti alloy and a piano wire.

The front side portion 30 has a first tapered portion 31, a small diameter portion 32, a second tapered portion 33, a third tapered portion 34, and a most distal portion 40 in this order from the main body portion 20 side toward the front end of the guidewire 10.

The first tapered portion 31 has a length of approximately 95 mm in the axial direction in the case of the present embodiment. The first tapered portion 31 is a tapered part having a circular cross-section and thinned toward the front end. In the present embodiment, the diameter of the first tapered portion 31 decreases from approximately 0.35 mm to approximately 0.21 mm in the front end direction.

The small diameter portion 32 is a cylindrical part having a circular cross-section and having a constant diameter. In the case of the present embodiment, the diameter of the small diameter portion 32 is approximately 0.21 mm.

The second tapered portion 33 and the third tapered portion 34 have circular cross-sections. The second tapered portion 33 and the third tapered portion 34 are in tapered shapes thinned toward the front end having different tilt angles from each other. In the case of the present embodiment, the diameter decreases from approximately 0.21 mm to approximately 0.04 mm in a direction from the end portion on the proximal side of the second tapered portion 33 to the end portion on the front side of the third tapered portion 34.

The layouts and dimensions of the aforementioned first to third tapered portions 31, 33, and 34 and small diameter portion 32 can be changed arbitrarily for the purpose of achieving desired stiffness or the like. For example, a cylindrical portion having a constant diameter can be provided between the second tapered portion 33 and the third tapered portion 34. Also, the number of the tapered portions and the angles of the tapered portions can be set arbitrarily as needed.

The most distal portion 40 has a first tapered flexible portion 41, a first columnar flexible portion 42, a second tapered flexible portion 43, and a second columnar flexible portion 44 in this order from the third tapered portion 34 side toward the front end of the guidewire 10 as shown in FIG. 2. In the present embodiment, the axial length of the most distal portion 40 is set to be approximately 16 mm.

The most distal portion 40 is a part having especially low flexural stiffness in the core shaft 14. Above all, the second columnar flexible portion 44 is a part having the lowest flexural stiffness.

The first tapered flexible portion 41 and the second tapered flexible portion 43 are tapered parts each having a circular cross-section and thinned toward the front end of the guidewire 10. The first columnar flexible portion 42 and the second columnar flexible portion 44 are cylindrical parts each having a circular cross-section and a constant diameter.

The first tapered flexible portion 41 is configured to decrease in diameter in a direction from the distal end of the third tapered portion 34 toward the first columnar flexible portion 42. In the case of the present embodiment, the diameter of the first columnar flexible portion 42 is set to be approximately 0.035 mm.

The second tapered flexible portion 43 is configured to decrease in diameter in a direction from the distal end of the first columnar flexible portion 42 toward the proximal end of the second columnar flexible portion 44. The diameter of the second columnar flexible portion 44 is set to be approximately 0.03 mm.

In the outer coil 60, the most distal portion 40 and the front end portion of the third tapered portion 34 of the core shaft 14 are surrounded by the inner coil 50. The inner coil 50 has two separate coils (a front inner coil portion 51 on the front side of the inner coil 50 and a rear inner coil portion 55 on the rear side of the inner coil 50) connected to each other. The front inner coil portion 51 surrounds the most distal portion 40 of the core shaft 14 while the rear inner coil portion 55 surrounds the front end portion of the third tapered portion 34 of the core shaft 14.

Each of the front inner coil portion 51 and the rear inner coil portion 55 is a hollow stranded coil manufactured by spirally winding plural metallic strands closely around a mandrel so as to substantially contact one another, thereafter eliminating residual stress at the time of the winding by a known heat treatment method, and taking out the mandrel.

The outer diameter of the front inner coil portion 51 is approximately 0.09 mm in the case of the present embodiment. The number of strands 51a of the front inner coil portion 51 is not particularly limited but is preferably 6 to 8. It is 8 in the case of the present embodiment. The diameter of the strand 51a used is approximately 0.02 to 0.03 mm and is approximately 0.02 mm in the case of the present embodiment.

The outer diameter of the rear inner coil portion 55 is approximately 0.15 mm in the case of the present embodiment. The number of strands 55a of the rear inner coil portion 55 is not particularly limited but is preferably 6 to 8. It is 6 in the case of the present embodiment. The diameter of the strand 55a used is approximately 0.02 to 0.04 mm and is approximately 0.03 mm in the case of the present embodiment.

Making the diameter of the strand 51a of the front inner coil portion 51 smaller than the diameter of the strand 55a of the rear inner coil portion 55 in this manner enables improvement in flexibility at the front portion of the inner coil 50.

Also, since the diameter of the strand 55a of the rear inner coil portion 55 located on the rear side is larger, torque transmissibility of the rear inner coil portion 55 can be increased. Accordingly, rotational torque and pushing torque (axial torque) transmitted from the rear side of the guidewire 10 can be transmitted to the front inner coil portion 51 efficiently. Thus, torque transmissibility of the guidewire 10 can be increased.

Also, the number of the strands 55a of the rear inner coil portion 55 is smaller than the number of the strands 51a of the front inner coil portion 51. This prevents the stiffness of the rear inner coil portion 55 having the larger outer diameter and diameter of the strand from being excessively higher than the stiffness of the front inner coil portion 51. Thus, since difference in stiffness occurring between the front inner coil portion 51 and the rear inner coil portion 55 can be alleviated, the torque transmissibility can be improved.

A material for the strands 51a and 55a is not particularly limited. In the case of the present embodiment, stainless steel is used. An example of the material other than this is a super elastic alloy such as an Ni—Ti alloy. Also, strands made of different materials can be combined.

It is to be noted that, in FIGS. 1 and 2, the diameter of the strand 51a of the front inner coil portion 51, the diameter of the strand 55a of the rear inner coil portion 55, and the diameter of a strand 60a of the outer coil 60 described later are shown with exaggeration in comparison with the axial dimension of the core shaft 14 to facilitate understanding.

The front end of the front inner coil portion 51 as well as the front end of the outer coil 60 is joined to the front end of the core shaft 14 by brazing coaxially with an axis of the core shaft 14. The brazed portion forms an approximately semispherical tip plug 15 (front end joint).

The rear end of the front inner coil portion 51 is coaxially joined to the first tapered flexible portion 41 of the most distal portion 40 by brazing. The brazed portion forms an inner intermediate joint 52.

The front end of the rear inner coil portion 55 as well as the rear end of the front inner coil portion 51 is coaxially joined to the first tapered flexible portion 41 of the most distal portion 40 at the inner intermediate joint 52. The inner intermediate joint 52 is not joined to the outer coil 60.

The rear end of the rear inner coil portion 55 is coaxially joined to the third tapered portion 34 by brazing. The brazed portion forms an inner rear end joint 56.

The tip portion of the guidewire 10 may be plastically deformed and bent when it contacts with a stenosis or passes through a tortuous vessel during operation. To prevent this, the inner coil 50 surrounds the most distal portion 40 and the front portion of the third tapered portion 34, which are thinned and have low flexural stiffness, at which such bending is easy to occur. Also, the range surrounded by the inner coil 50 almost corresponds to a range at which shaping is carried out. The shaping is conditioning to bend the tip portion of the core shaft 14 in a predetermined direction in advance.

Most of the core shaft 14 from the most distal portion 40 to the small diameter portion 32 is inserted in the outer coil 60. The outer coil 60 is made by winding a metallic strand 60a. The outer coil 60 has a coil main body portion 61, a tapered coil portion 64, and a front straight coil portion 63 in this order from the rear side of the outer coil 60 toward the front side.

The coil main body portion 61 is a part at which the strand 60a is wound to have a constant outer diameter. In the case of the present embodiment, the outer diameter is approximately 0.36 mm, and the axial length is approximately 120 mm. At the coil main body portion 61, the strand 60a is wound closely so that adjacent coils of the coil main body portion 61 substantially contact one another.

The tapered coil portion 64 is a part at which the strand 60a is wound to decrease the outer diameter toward the front end of the outer coil 60. In the case of the present embodiment, the outer diameter of the tapered coil portion 64 decreases from approximately 0.36 mm to approximately 0.2 mm. At the front side of the tapered coil portion 64, a gap 71 is formed between the inner circumferential surface of the tapered coil portion 64 and the outer circumferential surface of the rear side of the front inner coil portion 51. At the rear side of the tapered coil portion 64, a gap 75 is formed between the inner circumferential surface of the tapered coil portion 64 and the outer circumferential surface of the rear side of the rear inner coil portion 55.

The axial length of the tapered coil portion 64 is approximately 30 mm. At the tapered coil portion 64, the strand 60a is wound closely so that adjacent coils of the tapered coil portion 64 substantially contact one another.

The front straight coil portion 63 is a part at which the strand 60a is wound such that the front straight coil portion 63 has a constant outer diameter. In the case of the present embodiment, the outer diameter of the front straight coil portion 63 is approximately 0.2 mm, and the axial length is approximately 10 mm. The front straight coil portion 63 has on the rear side a close coiled portion 63a at which the strand 60a is closely wound so that adjacent coils of the front straight coil portion 63 substantially contact one another and on the front side an open coiled portion 63b at which the strand 60a is coarsely wound so as to have a gap between the adjacent coils of the front straight coil portion 63. The open coiled portion 63b increases flexibility at the front portion of the outer coil 60. In addition, as described later, the open coiled portion 63b alleviates interference between the front straight coil portion 63 of the outer coil 60 and the front inner coil portion 51 of the inner coil 50.

The strand 60a of the outer coil 60 is made of a radiopaque metal wire such as a platinum alloy. The diameter of the strand 60a is preferably approximately 0.05 to 0.06 mm and is approximately 0.05 mm in the case of the present embodiment.

It is to be noted that the strand 60a of the outer coil 60 may be constituted of a single strand into which a radiopaque metal wire such as a platinum alloy and a radiolucent metal wire such as stainless steel are joined. For example, a radiopaque coil may be used for an approximately 30 mm part on the front side of the outer coil 60 while a radiolucent coil may be used for the rest on the rear side.

As is apparent from the outer diameter of the front straight coil portion 63 and the diameter of the strand 60a, and the outer diameter of the front inner coil portion 51, a small gap exists between the inner circumferential surface of the front straight coil portion 63 and the outer circumferential surface of the front inner coil portion 51.

The front end of the outer coil 60 is joined by the tip plug 15 to the front end of the core shaft 14 by brazing coaxially with the front inner coil portion 51. The rear end of the outer coil 60 is coaxially joined to the small diameter portion 32 by brazing. The brazed portion forms an outer rear end joint 66.

Also, the outer coil 60 is joined at the rear end of the tapered coil portion 64 to the third tapered portion 34 by brazing. The brazed portion forms an outer intermediate joint 65.

It is to be noted that the outer intermediate joint 65 is preferably located inside the tapered coil portion 64. However, the outer intermediate joint 65 does not need to correspond to the rear end of the tapered coil portion 64. As described later, it is preferable for the outer intermediate joint 65 to be spaced from the inner rear end joint 56 of the rear inner coil portion 55 by a predetermined distance since this can prevent an abrupt change in stiffness.

The aforementioned inner intermediate joint 52 of the inner coil 50 is located further on the rear side than the proximal end of the close coiled portion 63a of the front straight coil portion 63 of the outer coil 60. Such an arrangement can prevent an abrupt change in stiffness of the guidewire 10 as much as possible. That is, the front straight coil portion 63 of the outer coil 60 has the open coiled portion 63b at which the strand 60a is coarsely wound. Thus, a change occurs in stiffness at a border between the open coiled portion 63b and the close coiled portion 63a at which the strand 60a is closely wound. Similarly, a change occurs in stiffness of the outer coil 60 at a border between the front straight coil portion 63 and the tapered coil portion 64 since the outer diameter of the outer coil 60 changes at the border. Overlapping of such borders at which the stiffness change occurs with the inner intermediate joint 52 of the inner coil 50 will result in emphasizing the stiffness change. Thus, in order to prevent this, it is preferable to make the inner intermediate joint 52 out of alignment with the border between the open coiled portion 63b and the close coiled portion 63a of the front straight coil portion 63 and the border between the front straight coil portion 63 and the tapered coil portion 64, as described above. Accordingly, the inner intermediate joint 52 is arranged to be displaced further on the rear side than the border between the front straight coil portion 63 and the tapered coil portion 64 (that is, further on the rear side than the proximal end of the close coiled portion 63a of the front straight coil portion 63).

It is to be noted that, in a case where the outer coil 60 does not have the front straight coil portion 63, and where the tapered coil portion 64 has an open coiled portion on the front side and a close coiled portion on the rear side, the inner intermediate joint 52 is preferably arranged to be displaced further on the rear side than a border between the open coiled portion and the close coiled portion.

The open coiled portion 63b of the front straight coil portion 63 contributes to preventing deterioration of flexibility at the front portion of the outer coil 60 caused by contact and interference between the front inner coil portion 51 and the front straight coil portion 63. That is, the open coiled portion 63b has a gap between the coils of the strand 60a. Hence, even if the front inner coil portion 51 contacts and interferes with the front straight coil portion 63 at a tortuous portion of a vessel, each coil of the strand 60a can slightly move in the axial direction. Accordingly, since the outer coil 60 is allowed to be curved, loss of flexibility at the outer coil 60 is prevented as much as possible.

Also, the inner rear end joint 56 of the inner coil 50 is spaced in the axial direction from the outer intermediate joint 65 of the outer coil 60. In a case where the inner coil 50 and the outer coil 60 are joined to the core shaft 14 at the same position, the stiffness of the guidewire 10 at the position will be high. In this case, the stiffness of the guidewire 10 abruptly changes. To prevent such an abrupt change in stiffness as much as possible, both the joints are spaced. This configuration can improve transmissibility of rotational torque and pushing torque given from the proximal side of the guidewire 10.

In the guidewire 10 of the present embodiment configured as above, the outer coil 60 has the tapered coil portion 64. This decreases the outer diameter of the outer coil 60. Accordingly, the guidewire 10 can enter a relatively serious narrow stenosis. In addition, providing the inner coil 50 can improve torque transmissibility. In other words, rotational torque and pushing torque transmitted from the proximal side of the guidewire 10 are transmitted to the front end of the guidewire 10 by the inner coil 50 via a long range including the rear inner coil portion 55 having a larger outer diameter and the front inner coil portion 51 having a smaller outer diameter.

Also, between the outer coil 60 and the inner coil 50, the gap 71 is secured between the front side of the tapered coil portion 64 having a smaller outer diameter and the rear side of the front inner coil portion 51 having a smaller outer diameter, and the gap 75 is secured between the rear side of the tapered coil portion 64 having a larger outer diameter and the rear side of the rear inner coil portion 55 having a larger outer diameter. In this manner, the gaps are secured between the inner circumferential surface of the outer coil 60 and the outer circumferential surface of the inner coil 50. Thus, even in a case where the guidewire 10 is rotated in a tortuous vessel or the like, mutual contact and interference between the outer coil 60 and the inner coil 50 are prevented as much as possible. This enables rotational torque to be transmitted to the front end of the guidewire 10 smoothly. This makes a rotational angle of the front end of the guidewire 10 correspond to a rotational angle given from the proximal side of the guidewire 10. That is, rotation followability of the guidewire 10 can be improved.

Also, in the guidewire 10 of the present embodiment, the diameter of the strand 55a forming the rear inner coil portion 55 located on the rear side of the inner coil 50 is larger than the diameter of the strand 51a forming the front inner coil portion 51. This can increase torque transmissibility of the rear inner coil portion 55. This can further improve flexibility at the front side of the inner coil 50 at which the front inner coil portion 51 is located. Also, in the guidewire 10 of the present embodiment, the number of the strands 55a of the rear inner coil portion 55 is smaller than the number of the strands 51a of the front inner coil portion 51. This prevents the stiffness of the rear inner coil portion 55 having the larger outer diameter and the large diameter of the strand from being excessively higher than the stiffness of the front inner coil portion 51. Thus, since difference in stiffness occurring between the front inner coil portion 51 and the rear inner coil portion 55 can be alleviated, the torque transmissibility can be improved.

Further, the inner intermediate joint 52 connecting the front inner coil portion 51 to the rear inner coil portion 55 joins the inner coil 50 to the core shaft 14. Accordingly, torque transmitted from the rear inner coil portion 55 can be transmitted to the core shaft 14 by the inner intermediate joint 52. Therefore, torque transmissibility is further improved. The inner intermediate joint 52 is arranged further on the rear side than the proximal end of the close coiled portion 63a of the front straight coil portion 63 of the outer coil 60. Thus, providing the inner intermediate joint 52 can prevent an abrupt change in stiffness of the guidewire 10 as much as possible. Accordingly, since the inhibition of torque transmission is prevented, torque transmissibility is improved.

Also, the most distal portion 40 and the third tapered portion 34, which are tip portions of the core shaft 14, are surrounded by the inner coil 50. Thus, the outer diameters of the most distal portion 40 and the third tapered portion 34 can be decreased without impairing the tip load. Consequently, when the tip portion of the guidewire 10 contacts with a serious stenosis in a vessel or enters a tortuous vessel, it is possible to prevent the tip portion of the guidewire 10 from being plastically deformed and not being restored in a bent or curved state as much as possible. That is, restorability of the guidewire 10 is improved.

Figure 3:
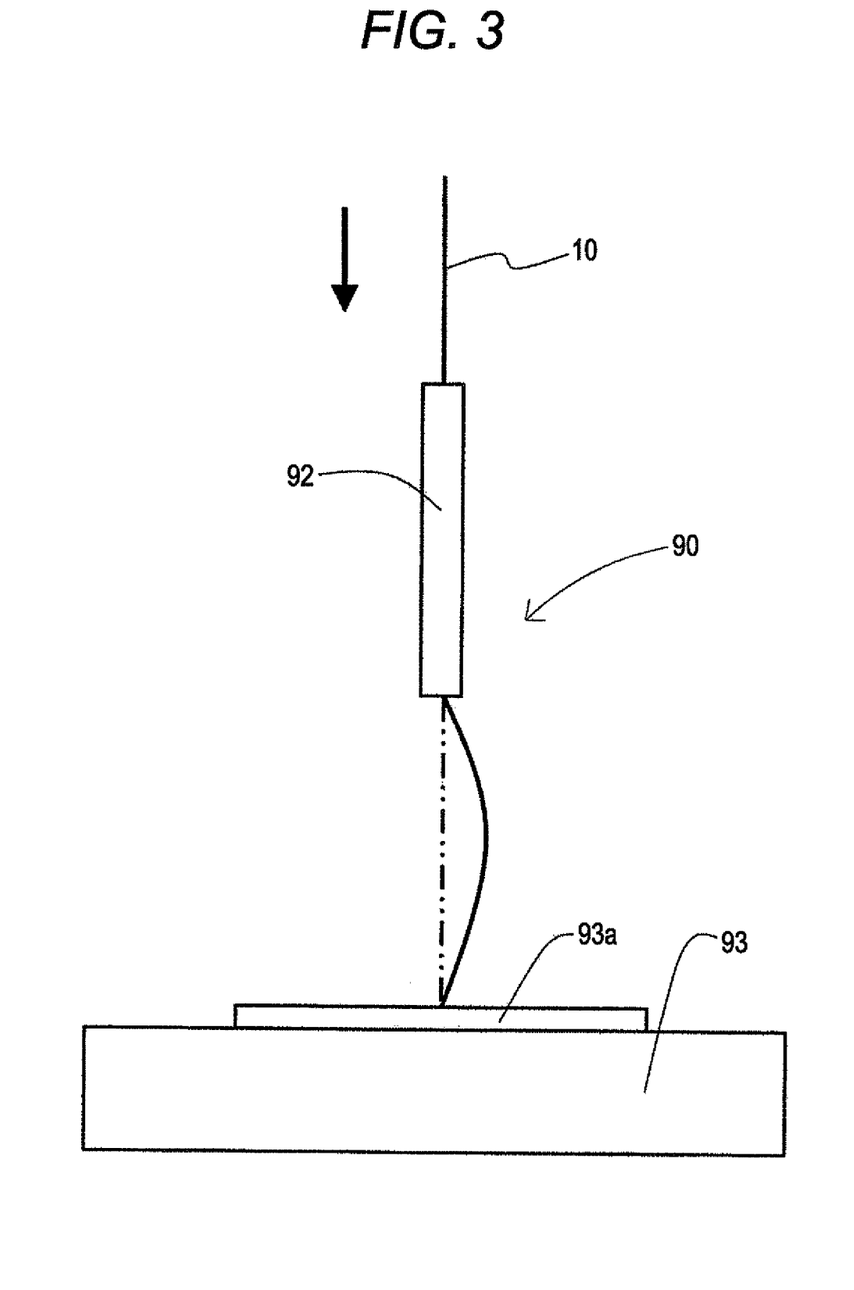
FIG. 3 illustrates an apparatus for measuring a tip load of the guidewire.

Meanwhile, a tip load is a maximum load that the front end of the guidewire 10 receives when the front end is pressed in the axial direction. For example, the tip load can be measured by a measuring apparatus 90 schematically shown in FIG. 3. The measuring apparatus 90 has a measuring portion 93a on a load measuring device 93 and a cylindrical supporting portion 92 arranged on its upper side to support the guidewire 10. In measurement by the measuring apparatus 90 configured as above, the guidewire 10 is first inserted into the supporting portion 92. Subsequently, the guidewire is mounted approximately vertically so that the front end of the guidewire contacts the measuring portion 93a. In this state, the guidewire 10 is pressed downward from the proximal side. By doing so, the measuring portion 93a is pressed by the front end of the guidewire 10. The maximum load at the time of this pressing is measured as a tip load. In the guidewire 10 of the present embodiment, the tip load measured by this measuring apparatus 90 is set to be approximately 5.0 [mN].

In the present embodiment described above, each of the front inner coil portion 51 and the rear inner coil portion 55 of the inner coil 50 is configured as the stranded coil including the plural strands. The stranded coil is highly advantageous in that it improves the tip load, torque transmissibility, and restoring force. However, both or either the front inner coil portion 51 and/or the rear inner coil portion 55 may be formed of a single-wire coil including one strand. Such a single-wire coil is preferably a close coiled coil in which adjacent coils of the strand substantially contact one another.

Also, in the present embodiment, the outer coil 60 has three portions: the coil main body portion 61, the tapered coil portion 64, and the front straight coil portion 63. However, the outer coil 60 may have a coil portion tapered to the front end without having the front straight coil portion 63.

In the present embodiment, the diameter of the strand 55a of the rear inner coil portion 55 is larger than the diameter of the strand 51a of the front inner coil portion 51 to increase torque transmissibility and improve flexibility at the front side of the inner coil 50. However, the diameter of the strand 55a of the rear inner coil portion 55 and the diameter of the strand 51a of the front inner coil portion 51 can be the same or similar.

Similarly, in the present embodiment, the number of the strands 55a of the rear inner coil portion 55 is smaller than the number of the strands 51a of the front inner coil portion 51 to alleviate difference in stiffness between the rear inner coil portion 55 and the front inner coil portion 51. However, the number of the strands 55a of the rear inner coil portion 55 and the number of the strands 51a of the front inner coil portion 51 can be the same.

Figure 4:
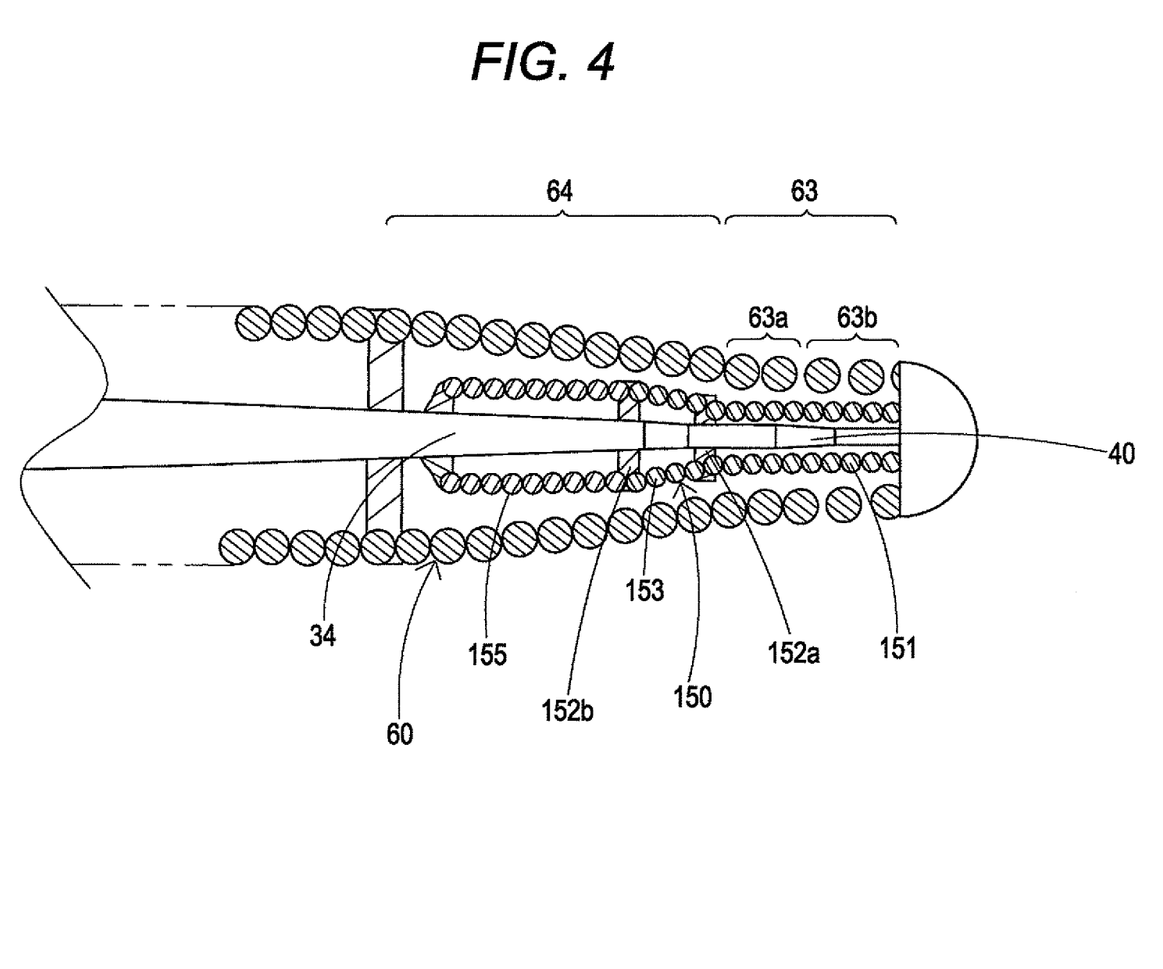
FIG. 4 illustrates a guidewire of a second embodiment.

In the present embodiment described above, the inner coil 50 has two coil portions: the front inner coil portion 51 and the rear inner coil portion 55, each of which has an approximately constant outer diameter. However, as in a second embodiment shown in FIG. 4, an inner coil 150 may be used. The inner coil 150 has three coil portions: a front inner coil portion 151 and a rear inner coil portion 155, each of which has an approximately constant outer diameter, and a tapered intermediate inner coil portion 153 connecting these two coil portions. In this case, the front inner coil portion 151 surrounds an entire length or most part of the most distal portion 40 of the core shaft 14, which is most thinned. On the other hand, the rear end portion of the rear inner coil portion 155 surrounds the front end portion of the third tapered portion 34, which is an adjacent part to the most distal portion 40 in the core shaft 14. The intermediate inner coil portion 153 surrounds a part between the part surrounded by the front inner coil portion 151 and the part surrounded by the rear inner coil portion 155.

In this configuration, the two cylindrical coil portions 151 and 155 can be connected smoothly by the intermediate inner coil portion 153. This enables smooth torque transmission. Also, in the configuration shown in FIG. 4, the three coil portions 151, 153, and 155 are joined to the core shaft 14 by a first inner intermediate joint 152a and a second inner intermediate joint 152b. Providing plural inner intermediate joints 152a and 152b in such a manner can further improve torque transmissibility. In this configuration as well, the first inner intermediate joint 152a is preferably arranged further on the rear side than the proximal end of the close coiled portion 63a of the front straight coil portion 63 of the outer coil 60. This can prevent an abrupt change in stiffness of the guidewire as much as possible.

Figure 5:
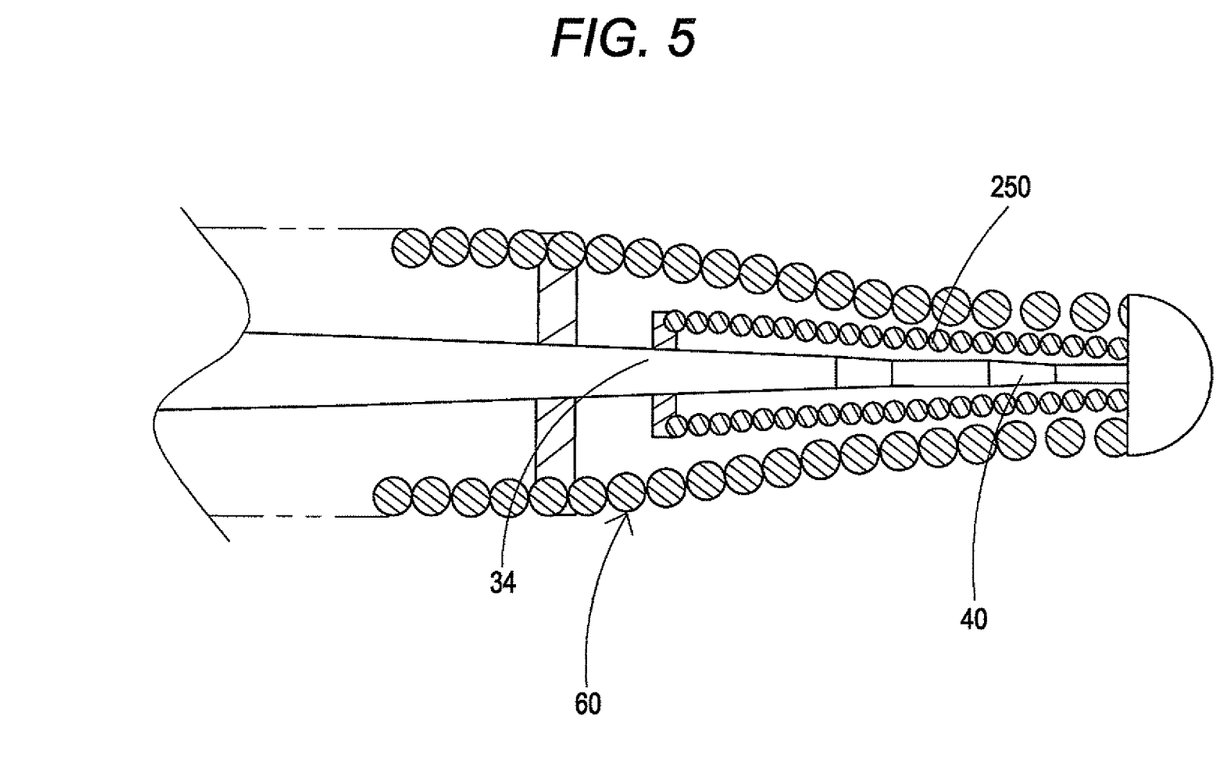
FIG. 5 illustrates a guidewire of a third embodiment.

Also, as in a third embodiment shown in FIG. 5, an inner coil 250 may be used. The inner coil 250 includes one tapered stranded coil having a diameter that gradually decreases toward the front end of the inner coil 250. In this case as well, the tip portion of the inner coil 250 surrounds the most distal portion 40 of the core shaft 14, which is most thinned. In addition, the rear end portion of the inner coil 250 surrounds the front end portion of the third tapered portion 34, which is an adjacent part to the most distal portion 40 in the core shaft 14.

In this configuration, a change in stiffness of the inner coil is reduced as much as possible as compared with a case of using an inner coil including plural coil portions. Since this enables smooth torque transmission, torque transmissibility in the rotational direction and axial direction of the guidewire can be improved.

In the third embodiment, it is preferable to make the cross-sectional area of the strand located on the front side of the inner coil 250 smaller than the cross-sectional area of the strand located on the rear side. This can improve flexibility at the front portion of the inner coil 250. Also, with this configuration, the cross-sectional area of the strand located on the rear side is larger. Accordingly, rotational torque and pushing torque transmitted from the rear side of the guidewire can be transmitted to the front side efficiently. Thus, torque transmissibility of the guidewire can be increased.

Examples of a method for making the cross-sectional area of the strand on the front side of the inner coil 250 smaller than the cross-sectional area of the strand on the rear side of the inner coil 250 include a method of centerless grinding on an external surface on the front side and a method of electrolytic polishing to make the diameter of the strand on the front side smaller.

In the aforementioned embodiments, the most distal portion 40 has the first tapered flexible portion 41, the first columnar flexible portion 42, the second tapered flexible portion 43, and the second columnar flexible portion 44, any of which has a circular cross-section. However, the tip portion of the most distal portion 40 may have one or plural flat parts formed by press working.

Applying press working to the tip portion of the most distal portion 40 in such a manner brings about an effect of improvement in flexibility and torsional stiffness of the tip portion.

Also, the guidewire of the present embodiment can be used for a brain and other organs as well as for a heart.

While the invention has been shown and described in detail, the foregoing description is in all aspects illustrative and not restrictive. It is therefore understood that numerous modifications and variations can be devised without departing from the spirit and scope of the invention.

The invention claimed is:

1. A guidewire comprising:
   a core shaft;
   an outer coil having a tapered coil portion constituted by at least one strand wound to decrease an outer diameter toward a front end of the core shaft and surrounding a front side portion of the core shaft;
   an inner coil constituted by at least one strand wound, which surrounds the front side portion of the core shaft entirely within the outer coil, and whose outer diameter on a front side, arranged on a front side of the tapered coil portion, is smaller than an outer diameter on a rear side, wherein a gap is disposed between the inner coil and the outer coil and the gap increases towards the rear end of the core shaft;
   a front end joint joining a front end of the outer coil and a front end of the inner coil to the front end of the core shaft;
   an outer rear end joint joining a rear end of the outer coil to the core shaft; and
   an inner rear end joint joining a rear end of the inner coil to the core shaft further on a front side than the outer rear end joint.

2. The guidewire according to claim 1, wherein the inner coil includes:
   a front inner coil portion which is arranged on a front side of the inner coil and constituted by at least one strand wound such that the front inner coil portion has an approximately constant outer diameter; and
   a rear inner coil portion which is arranged on a rear side of the inner coil, constituted by at least one strand wound such that the rear inner coil portion has an approximately constant outer diameter, and which has a larger outer diameter than the outer diameter of the front inner coil portion.

3. The guidewire according to claim 2, wherein a diameter of the strand constituting the front inner coil portion is smaller than a diameter of the strand constituting the rear inner coil portion.

4. The guidewire according to claim 2, wherein
   the front inner coil portion and the rear inner coil portion of the inner coil are joined to each other by an inner intermediate joint, and
   the inner intermediate joint joins the inner coil to the core shaft.

5. The guidewire according to claim 4, wherein
   the outer coil has a front straight coil portion having an approximately constant outer diameter on a front side of the tapered coil portion, and
   the inner intermediate joint is located further on a rear side than a border between the front straight coil portion and the tapered coil portion.

6. The guidewire according to claim 5, wherein the front straight coil portion has an open coiled portion at which coils are spaced from one another on a front side of the front straight coil portion and a close coiled portion at which coils substantially contact one another on a rear side of the front straight coil portion.

7. The guidewire according to claim 2, wherein at least one of the front inner coil portion and the rear inner coil portion has a hollow stranded coil made by winding a plurality of strands.

8. The guidewire according to claim 7, wherein the rear inner coil portion is constituted by a smaller number of strands than the front inner coil portion.

9. The guidewire according to claim 1, wherein the inner coil is constituted by a single coil made by winding at least one strand to have an outer diameter that gradually decreases toward the front end of the core shaft.

10. The guidewire according to claim 9, wherein a cross-sectional area of the strand on a front side of the inner coil is smaller than a cross-sectional area of the strand on a rear side of the inner coil.

11. The guidewire according to claim 1, wherein the inner coil is a hollow stranded coil made by winding a plurality of strands.

* * * * *